United States Patent [19]
Johnson

[11] Patent Number: 5,611,333
[45] Date of Patent: Mar. 18, 1997

[54] DILATOR WITH PEEL FORCE REDUCING STRUCTURE

[75] Inventor: Bruce C. Johnson, St. Paul, Minn.

[73] Assignee: Creative Integration & Design, Inc., St. Paul, Minn.

[21] Appl. No.: 574,450

[22] Filed: Dec. 15, 1995

[51] Int. Cl.⁶ .......................... A61M 29/00; A61M 15/00; A61F 5/08; A62B 7/00
[52] U.S. Cl. ................ 128/200.24; 128/207.18; 128/848; 606/199; 606/204.45; 602/74; 602/54
[58] Field of Search ............... 128/200.24, 207.18, 128/912, 848, DIG. 26; 606/199, 204.45; 602/74, 41, 47, 54, 55, 56, 57–59, 902

[56] References Cited

U.S. PATENT DOCUMENTS

| | | |
|---|---|---|
| 850,978 | 4/1907 | Soares . |
| 1,043,924 | 11/1912 | Gottlieb ................................. 606/199 |
| 1,292,083 | 1/1919 | Sawyer . |
| 1,950,839 | 3/1934 | Chirila . |
| 2,001,862 | 5/1935 | Battey . |
| 2,398,073 | 4/1946 | Bonde . |
| 2,509,157 | 5/1950 | Lind . |
| 2,566,148 | 8/1951 | Sky . |
| 2,586,219 | 2/1952 | Geffas . |
| 2,625,931 | 1/1953 | Phillips . |
| 3,046,989 | 7/1962 | Hill . |
| 3,426,751 | 2/1969 | Radewan . |
| 3,531,090 | 9/1970 | Laible . |
| 3,742,943 | 7/1973 | Malmin . |
| 3,835,848 | 9/1974 | Berner . |
| 3,935,859 | 2/1976 | Doyle . |
| 4,153,051 | 5/1979 | Shippert . |
| 4,213,452 | 7/1980 | Shippert . |
| 4,274,402 | 6/1981 | Shippert . |
| 4,340,040 | 7/1982 | Straith . |
| 4,402,314 | 9/1983 | Goode . |
| 4,414,977 | 11/1983 | Rezakhany . |
| 4,534,342 | 8/1985 | Paxa . |
| 4,674,133 | 6/1987 | Oschner . |
| 4,823,789 | 4/1989 | Beisang, III ...................... 128/207.18 |
| 4,932,943 | 6/1990 | Nowak ........................... 238/DIG. 26 |
| 4,971,282 | 11/1990 | Dickinson ........................... 248/231.8 |
| 4,984,302 | 1/1991 | Lincoln ..................................... 2/206 |
| 4,995,114 | 2/1991 | Price, Jr. ..................................... 2/15 |
| 5,003,971 | 4/1991 | Buckley . |
| 5,022,389 | 6/1991 | Brennan . |
| 5,101,837 | 4/1992 | Perrin . |

FOREIGN PATENT DOCUMENTS

| | | |
|---|---|---|
| 437661 | 11/1926 | Germany . |
| 453006 | 3/1928 | Germany . |
| 12987 | 9/1909 | United Kingdom . |

OTHER PUBLICATIONS

Pp. 11 and 12 of Specification Sheet of CoNco entitled "Nasal Splint—Disposable Glove".
Copy of Packaging containing a Nasal Strip sold prior to the filing of this application by Bolinger Industries.

*Primary Examiner*—Kimberly L. Asher
*Attorney, Agent, or Firm*—Kinney & Lange, P.A.

[57] ABSTRACT

A dilator formed with a truss with a pair of spaced-apart end surfaces that provides a restoring force therebetween if forced toward one another, this restoring force provided by a resilient band extending between the opposite ends of the truss with a plurality of notches located at each of the ends thereof. The notches exceed at least a third of the thickness of the band and may comprise a separation at the location thereof between selected portions of said first resilient band with this separation surrounded by a corresponding separation edge thereabout intersecting a first surface of the first resilient band. A second and similar band may also be provided in the truss.

18 Claims, 10 Drawing Sheets

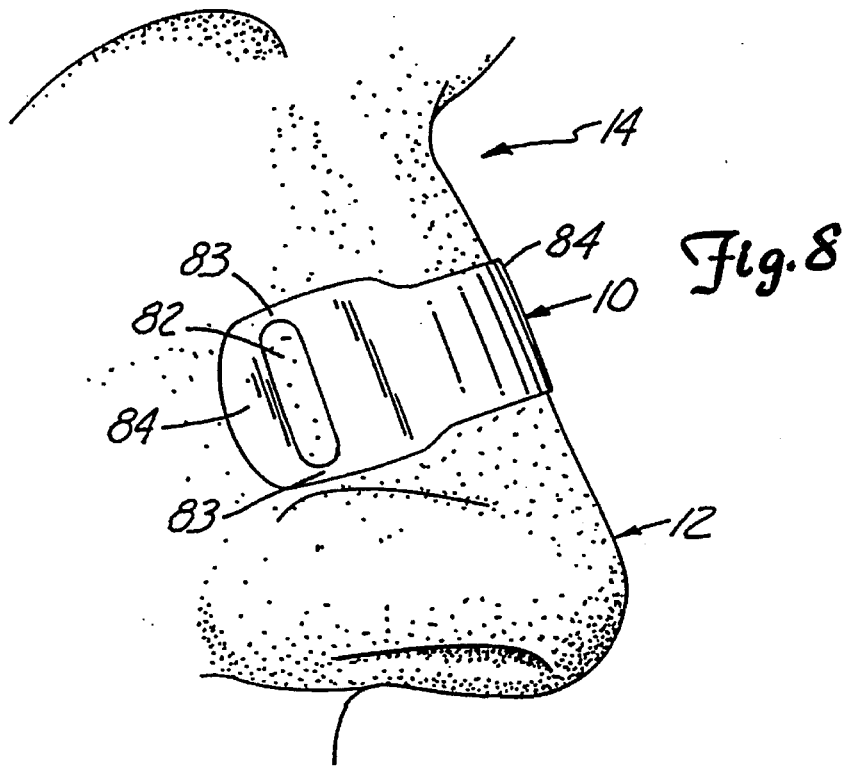
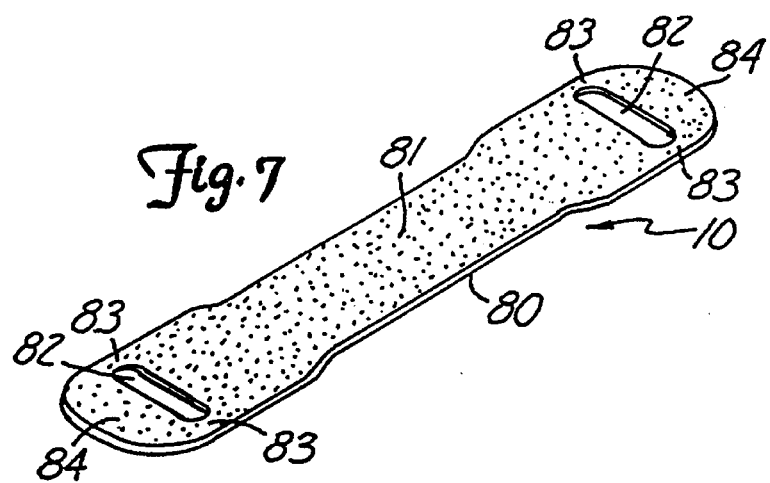
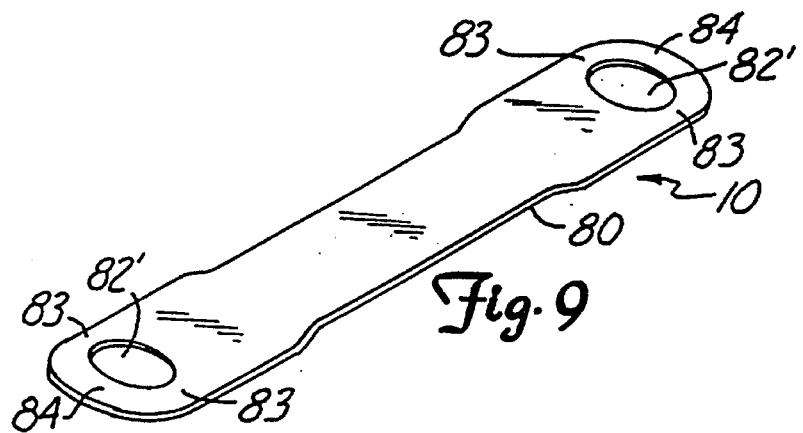

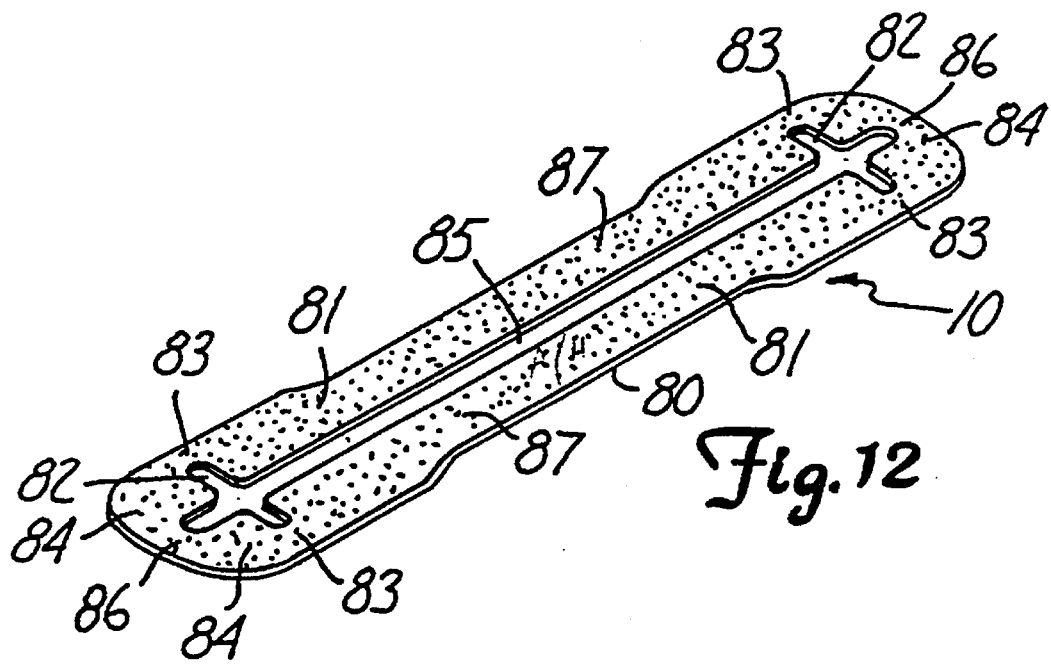
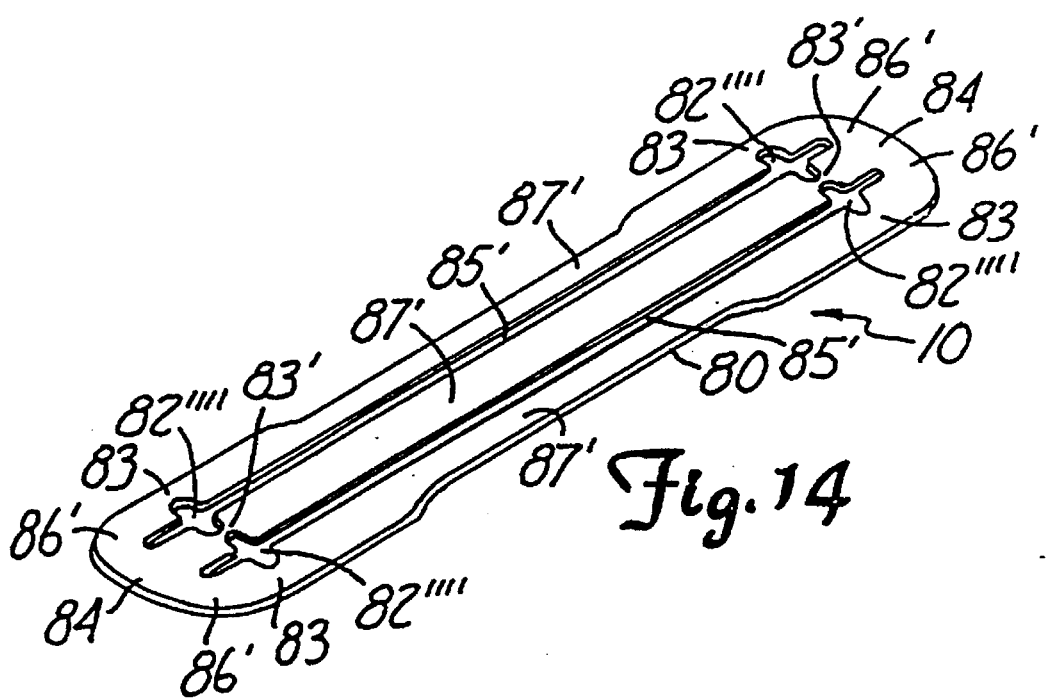

DILATOR WITH PEEL FORCE REDUCING STRUCTURE

BACKGROUND OF THE INVENTION

The present invention relates to devices for separating bodily tissues and, more particularly, to devices for separating outer wall tissues from inner structure tissues to dilate nasal passages of a human nose.

Humans are often subject to interior obstructing of their nasal passages which makes breathing more difficult. Examples of such obstructing are a deviated septum typically resulting from injury to the nose, swelling of interior nose tissues due to allergic reactions, and the nasal symptoms present in those suffering with the common cold. The lower portion of a nostril, immediately interior the entrance to the nostril, is known as a vestibule. The vestibule tapers inwardly to a narrowed neck-like area called the nasal valve. Nasal passages, posterior to the nasal valve, widen again. Nasal obstructions commonly occur at the nasal valve to the point that the nasal valve may be substantially blocked. Commonly, the lateral wall (i.e., the outer wall tissues partially about the nasal passage) at the nasal valve is loose with the result that the outer wall tissues draw in during the inhalation portion of the breathing process to substantially or completely block passage of air through the nasal passage particularly if such obstruction is present.

Blockage of the nasal passage is obviously an irritation and a possible detriment to persons who experience it. In particular, sustained mouth breathing over a long period of time may cause lung irritation due to the inhalation of foreign particles that would otherwise be filtered if the breath had passed through the nose. Blockage of the nasal passage is particularly uncomfortable at night, since it is uncomfortable for many people that have a problem to breathe through their mouth while asleep. Nasal blockages can lead to sleep disturbances, sleep irregularities, or snoring or a combination thereof. In addition, a person with such a condition may wake often because that person is not easily inhaling sufficient quantities of oxygen.

Where the cause of the obstruction in the nasal passage is due to structural problems such as a deviated septum or an unusually small valve opening, and where the effect on breathing is relatively serious, a common resort is to surgically attempt to correct the malformation of the nasal passages. However, surgery is expensive and may not ultimately correct the problem. Where the cause is allergies or the common cold, another alternative often used is a medicated spray to reduce the associated swelling of tissues along the nasal passages. This treatment too often was insufficient to alleviate the problem, and there are possible detrimental effects on the tissues themselves with long-term use.

Because of these shortcomings experienced using these methods, mechanical aids termed nasal dilators have been used in attempts to open nasal passages. Such dilators have been both of the internal variety which in effect push out the sides of the nasal passages to open them, and of the external variety effectively pulling on some of those sides. The internal types, which require insertion in the nasal passages, may irritate them and result in an itching feeling. Because of the large variety of geometries encountered in human nasal passages, these nasal dilators often must be specifically designed for each particular user. External nasal dilators have either been securely adhered to the user's nose (requiring some aid to remove) but adjustable with respect to the force of the pull on the outer wall tissues, or have been removably adhered to the user's nose but unadjustable single body items which provide a force pulling on wall tissues determined by the single body structure. The former are difficult to remove and difficult to adjust to provide a proper force which yields sufficient expansion of the wall tissues without the mechanical arrangement for doing so becoming disengaged, knocked askew during ordinary use, or the like.

Single body external nasal dilators have had designs developed therefor which provide a satisfactory outwardly pulling force on tissues being dilated without discomfort, and which can also be relatively easily put in place for use as a dilator while yet being relatively easily removed. This latter feature has been accomplished in dilators using spring containing bodies with pressure sensitive adhesives, and the peel forces, which are generated by the relatively stiff spring ends along with motion of the skin under and adjacent to such dilators adhered thereto using such adhesives, has been prevented from causing the dilators to separate from the skin through a suitable geometry at the ends thereof. One possibility is to use spring members in the dilator body which are of shorter length than the length of the body in which they are contained so that centering the position of such spring members in that body leaves each of the spring member ends spaced apart from the corresponding body ends. This possibility was shown in earlier filed copending U.S. Patent Application by B. C. Johnson entitled "Nasal Dilator" having Ser. No. 08/183,916 and filed on Jan. 19, 1994 which is hereby incorporated herein by reference. In effect, the portions of the body ends past the spring members ends serve as body extensions that resist the peel forces occurring at the ends of these spring members. Unfortunately, the need to individually position spring members during the manufacturing process is expensive and subject to errors.

Alternatively, the central end portions of the dilator body at the opposite ends thereof past the spring member ends can be cut out during manufacture so that the end edges reach back to the ends of the short spring members or, more practically, the springs, rather than being short and positioned, can extend for the length of the dilator body before being cut into units with the central end portions being cut out along with the cutting into units. This will leave body side extensions without any spring member portions therein, and these side extensions will extend past the ends of the spring members after such cutting as described in earlier filed copending U.S. Patent Application by W. J. Doubek, D. E. Cohen and B. C. Johnson entitled "Nasal Dilator" having Ser. No. 08/070,554 and filed on Apr. 20, 1993 which is hereby incorporated herein by reference. However, the adhering extensions used in the geometry of the dilator ends described there to prevent that dilator from peeling away from the skin restrict the possible end shapes which might otherwise be used and, because such extensions do extend past the spring members in the dilator body, they unavoidably result in some waste of material in the manufacturing process. This situation can be eased by eliminating any central end portions being cut out and, instead, just providing relief cuts between the spring members and the side extensions portions. Such an arrangement, however, will result in a small amount of peeling of the central end portions not cut out as they were in the previous version. The resulting peeled away central end portions will be subject to catching onto objects brought into contact with, or near to, the wearer's nose, collecting dirt, becoming unsightly, causing itching, etc.

In addition, the skin under those extensions accumulates some moisture therein due to the reduced evaporation therefrom resulting from the presence of the extensions over that skin which weakens the structure thereof at such locations. At dilator removal, the forces between the dilator extensions and the skin change from being primarily peel forces to being primarily sheer forces which are much greater in magnitude due to the nature of the pressure sensitive adhesive used on the extensions, and so there is a potential for damaging the weakened skin upon the introduction of the greater magnitude of sheer forces during removal of those extensions from the skin.

On the other hand, the omission of the extensions or any relief cuts between the spring force member and the adjacent side portions of the dilator leads to the spring members reaching the extreme end edges of the dilator. The substantially constant spring force along the dilator from end edge to end edge provided by the resilient members therein, along with the relatively high stiffness of short sections of the spring back from the end edges, leads to the occurrence of peel forces due to the motion of the skin beneath the dilator during ordinary use that are sufficient in a significant number of dilator uses to cause the ends of the dilator to begin to disengage from the skin of the user therebeneath. Thus, there is a desire for a single body dilator structure that reduces waste in manufacture, allows design freedom for the ends of dilators, and reduces the risk of skin damage during separation of the dilator from the user's skin.

SUMMARY OF THE INVENTION

The present invention provides a dilator which in use tends to force wall tissues in the human body, on which it is engaged under force, away from one another. The dilator comprises a truss having a pair of spaced-apart end surfaces which provides a restoring force tending to separate those surfaces if they are forced toward one another. The end surfaces have engagement means adhered thereto which can engage exposed surfaces of such outer wall tissues sufficiently to remain engaged against such restoring force. This restoring force is provided in part by at least a first resilient band of a selected thickness extending between end edges of the opposite ends of the truss, adjacent the end surfaces, where this band has a plurality of notches located therein exceeding at least a third of that thickness which are directed across the band to reduce the restoring forces at those locations. Such a notch may comprise a separation at the location thereof between selected portions of said first resilient band with this separation surrounded by a corresponding separation edge thereabout intersecting a first surface of the first resilient band. These notches can be in two groups near the opposite end edges of the resilient band in the truss with the deepest or largest notches closest to the ends and the others getting successively less deep or smaller in sequence toward the middle of the truss. A second resilient band can also be provided in the truss spaced apart entirely or mostly from the first resilient band to also extend between the end edges thereof, and which also has notches provided therein.

BRIEF DESCRIPTION OF THE DRAWINGS

FIG. 7 shows a pictorial view of an alternate embodiment of the dilator of the present invention;

FIG. 8 shows a pictorial view of a portion of a human face including the nose, and of the dilator of FIG. 7 engaged with that nose;

FIG. 9 shows a pictorial view of an alternate embodiment of the dilator of the present invention;

FIG. 12 shows a pictorial view of an alternate embodiment of the dilator of the present invention;

FIG. 14 shows a pictorial view of an alternate embodiment of the dilator of the present invention;

DETAILED DESCRIPTION OF THE PREFERRED EMBODIMENTS

Figure 1:
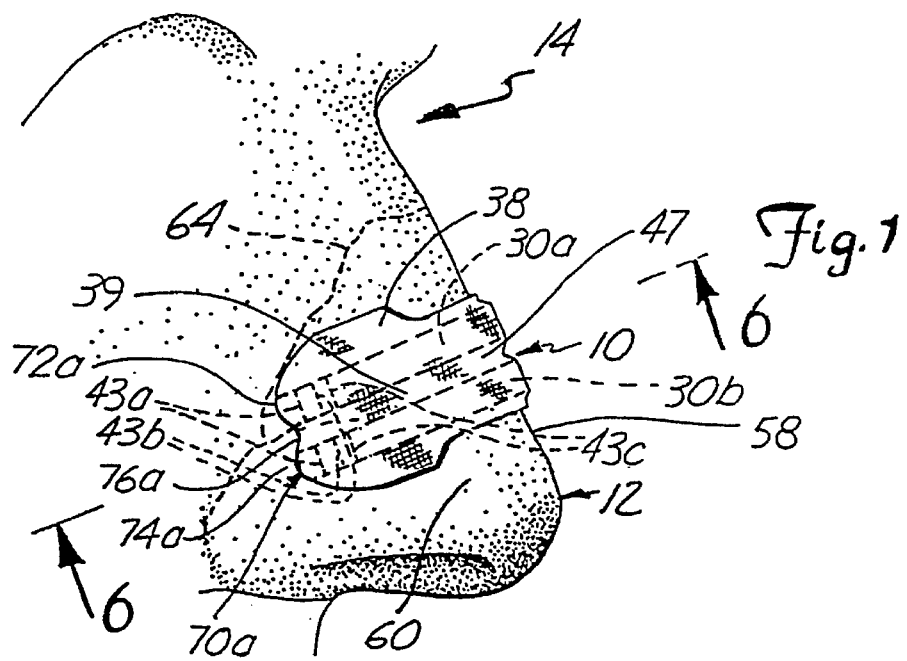
FIG. 1 shows a pictorial view of a portion of a human face including the nose, and of a dilator embodying the present invention engaged with that nose.

A dilator, 10, embodying the present invention is shown in FIG. 1. Dilator 10 is shown being used as a nasal dilator on a subject in being engaged with a nose, 12, seen as part of a portion of a human face, 14.

Figure 2A:
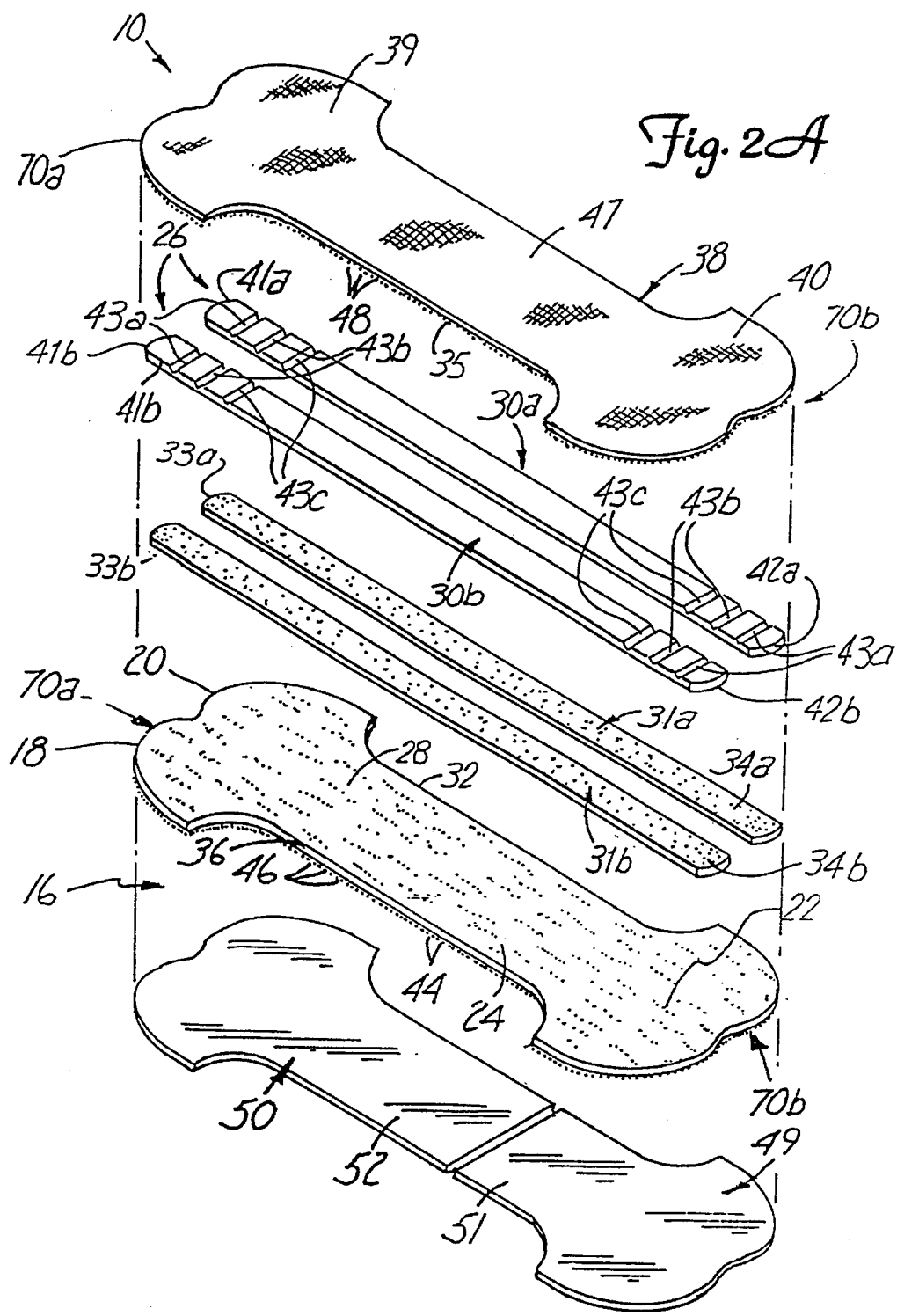
FIG. 2A shows an exploded pictorial view of components of the dilator of the present invention shown in FIG. 1.

The elements used in the construction of dilator 10 can be seen in the exploded pictorial view of that dilator shown in FIG. 2A. As seen there, dilator 10 comprises a unitary, or single body, truss member, 16, having a strip of base material, 18, with a first end region, 20, and a second end region, 22, joined to first end region 20 by an intermediate segment, 24. The width of intermediate segment 24 is less than the width of first and second end regions 20 and 22 for the comfort of the user because of covering less of the user's skin. Base material 18 is preferably formed of a polyester fabric that allows the skin on user nose 12 to exchange gases with the atmosphere relatively easily to maximize comfort and minimize irritation during use. A suitable, nonwoven, spun-laced, 100 percent polyester fabric from which to form base material 18 is available from E. I. DuPont Nemours & Co. under the trade name SONTARA®. SONTARA® fabric typically has a breaking strength property in a ratio of approximately 2:1 as determined by the machine direction (MD) or warp, relative to the cross direction (XD) or fill, of the fabric. In addition, SONTARA® fabric typically has an elongation percentage ratio of approximately 3:1 as determined by the resulting elongations for equal forces in the cross and machine directions of the fabric. The machine direction of the fabric is parallel to the longitudinal extent of base material 18.

Truss 16 further includes resilient means, 26, secured to a first side, 28, of base material 18. Resilient means 26 includes a first resilient band, 30*a*, and a second resilient band, 30*b*. First resilient band 30*a* has a first end, 41*a*, and a second end, 42*a*. Second resilient band 30*b* has a first end, 41*b*, and a second end, 42*b*. First and second resilient bands 30*a* and 30*b* are each formed of a polymer material. For example, an industrial grade, biaxially oriented polyester such as MYLAR® Type A offered by E. I. DuPont Nemours & Co. which is cut to approximately 0.080 in. to 0.135 in. in width from 0.010 in. thick stock has been found suitable. Using a polymer material which is relatively thin as just described for each of first and second resilient bands 30*a* and 30*b* enhances the axial, torsional flexibility of each of these bands about the longitudinal extent of each depending on the width of the bands actually used.

A sequence of three notches, 43*a*, 43*b*, and 43*c*, is shown in each of first and second resilient bands 30*a* and 30*b*. Notches 43*a*, nearest the extreme ends of each of first and second resilient bands 30*a* and 30*b*, is the deepest notch and, for example, in a resilient band with a 2.60 in. length and a 0.135 in. width, this notch would be typically 0.15 in. inward from the resilient band end nearest thereto with a depth of 80% to 100% of the thickness of that resilient band, typically 90% to 100% of the thickness. The next notches inward in this example, notches designated 43*b*, would be each located 0.10 to 0.20 in. closer to the middle with a depth of 60% to 90% of the resilient band thickness, typically 70%. Finally, the last notch shown in each sequence and closest to the middle of the resilient band, notches designated 43*c*, would typically be another 0.10 to 0.20 in. closer to the middle but with a depth of only 40% to 70% of the resilient band thickness, typically around 40%.

Further notches could be included in sequence extending closer to the middle of the corresponding resilient bands, and different depths for each of the notches could be used. The effect of introducing these notches ever less deep in the sequence thereof toward the middle is to monotonically decrease, or taper off, the effective spring constant along the two half-lengths of each of the resilient bands starting from the middle thereof. The deepest notches reduce effective spring constant the most so that locating them at the ends of the bands is quite effective in reducing the peel forces at the ends of the resilient bands resulting from the bands spring force and the motion of the skin therebeneath. The other notches of lesser depth as one proceeds to go to the center of the band reduced the spring constant less at each location thus giving an increasing effective spring constant along the directions from the ends of the resilient bands toward the center. As a result, the desired pull on the outer wall tissues of the user's nose can be set by the type of material, length, thickness and width to provide the desired pull on those tissues while being reduced sufficiently to, as will be described, avoid undue peel forces occurring between the pressure sensitive adhesive beneath the ends of these bands and the skin to which it is attached.

First and second resilient bands 30*a* and 30*b* are secured by first and second flexible strips of interface adhesive material, 31*a* and 31*b*, to a first side, 28, of base material of strip 18. First interface adhesive material strip 31*a* has a first end, 33*a*, and a second end, 34*a*. Second interface adhesive material strip 31*b* has a first end, 33*b*, and a second end, 34*b*. First and second strips of interface adhesive material 31*a* and 31*b* are of the same shape and size in the plan view thereof as are first and second resilient bands 30*a* and 30*b*, respectively, in a plan view thereof.

First resilient band 30*a* is secured by adhesive material strip 31*a* to base material strip 18 adjacent a first edge, 32, of intermediate segment 24 thereof. Second resilient band 30*b* is parallel to, and spaced apart from, first resilient band 30*a*, and is secured by adhesive material strip 31*b* to base material strip 18 adjacent a second edge, 36, of intermediate segment 24 thereof. First and second resilient bands 30*a* and 30*b* are oriented, as stated above, generally parallel to one another and substantially parallel to the longitudinal extent of base material strip 18. Each of interface adhesive material strips 31*a* and 31*b* is preferably an acrylic, pressure sensitive bio-compatible transfer tape adhesive material such as that designated 3M 1509 offered by, and available from, Minnesota, Mining & Manufacturing Company, Inc., or an acrylic, pressure sensitive bio-compatible transfer adhesive material such as that designated 1368B offered by, and available from, the Betham Corporation or such as that designated 1524 offered by, and available from, Minnesota, Mining & Manufacturing Company, Inc.

Truss 16 further includes a flexible strip of top material, 38, having a first end region, 39, a second end region, 40, and an intermediate segment, 47, with the same size and shape in plan view as base material strip 18 has in plan view. A bottom surface 35, of top material strip 38 includes a layer of an adhesive substance, 48, that extends over the first and second end regions 39 and 40 and over an intermediate segment 47 thereof. Adhesive substance 48 is a porous, acrylic, pressure sensitive bio-compatible adhesive. Top material strip 38 covers first and second resilient bands 30*a* and 30*b* and first side 28 of base material strip 18, and is secured thereto by adhesive substance layer 48.

Top material strip 38 aids in preventing first and second resilient bands 30*a* and 30*b* from separating from base material strip 18 and interface adhesive material strips 31*a* and 31*b* in those situations where truss 16 is flexed by movement of that skin thereunder on which it is being used. In addition, top material strip 38 limits to stone degree base material strip 18 by together providing a stiffer material in the major plane thereof to provide a geometrically more stable combination which permits installing and removing dilator 10 more easily. Top material strip 38 is preferably a porous, nonwoven material with adhesive substance 48 provided thereon such as that designated 3M 1533 offered by, and available from, Minnesota, Mining & Manufacturing, Inc.

Figure 2B:
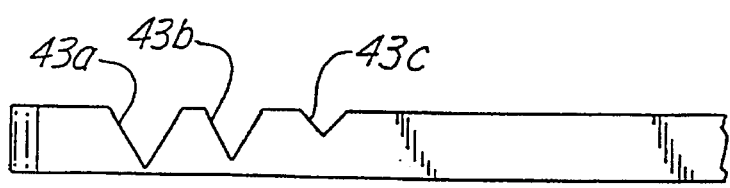
FIG. 2B shows a fragmentary view of a portion of FIG. 2A.

Further in connection with base material strip 18 in FIG. 2, a second side, 44, thereof has a layer of an adhesive substance, 46, extending over it including over first and second end regions 20 and 22 and over intermediate segment 24 on that side thereof. Adhesive substance 46 is a porous, acrylic, pressure sensitive bio-compatible adhesive. Adhesive 46 is used to engage dilator 10 with the skin of the outer wall tissue on which that dilator is to be used, the outer wall of nose 12 in FIG. 1. A fabric suitable for forming base material strip 18 can be obtained with adhesive substance 46 provided thereon such as the material 3M 1776 offered by, and available from, Minnesota Mining & Manufacturing, Inc.

Adhesive substance 46 is covered before use by a pair of release liners including a first release liner, 49, and a second release liner, 50. These release liners cover adhesive substance 46 on first end region portion 20 and second end region portion 22 of base material strip 18 with an extended portion, 51, of first release liner 49 and an extended portion, 52, of second release liner 50 covering the adhesive substance 46 portion on intermediate segment 24 of base material 18. First and second release liners 49 and 50 are readily removable from adhesive substance 46.

Figure 3:
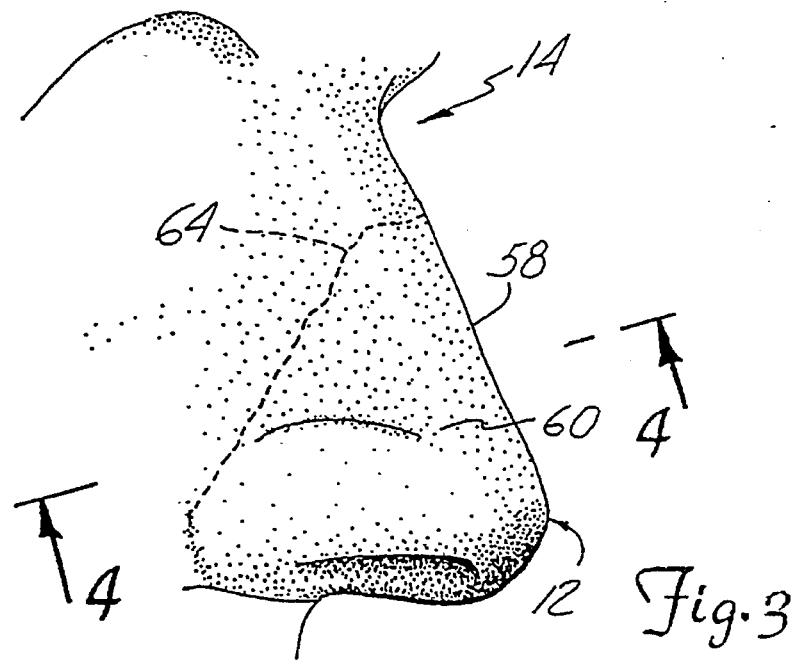
FIG. 3 shows a pictorial view of the same portion of the human face shown in FIG. 1 absent any dilator.
Figure 4:
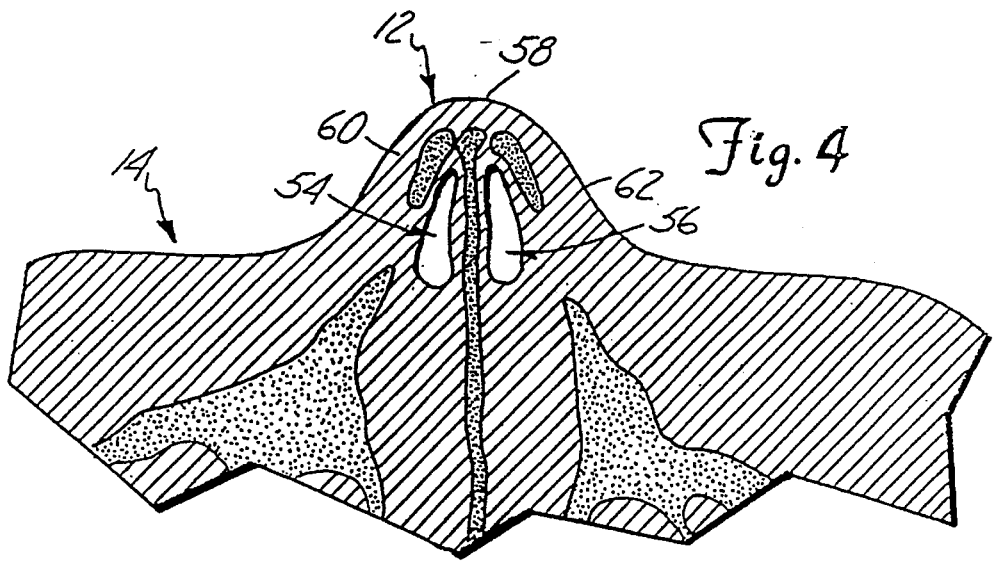
FIG. 4 shows a cross section view taken from the view of FIG. 3 with the nose shown being in a state of relatively little flow of air through the nasal passages.

As can be seen in FIGS. 3 and 4, a human nose 12 includes a first nasal passage, 54, a second nasal passage, 56, and a portion of nose 12 generally referred to as a bridge, 58, of that nose, extending between but outside of first and second nasal passages 54 and 56. The state of the nasal passages in FIG. 4 is that occurring in the portion of the breathing cycle in which there is little airflow occurring therethrough, and are the nasal passages of a person that is neither sick with an ailment which has symptoms involving the nasal passages nor has had nasal passage injury. Thus, nasal passages 54 and 56 are relatively open and can easily pass airflows.

Figure 5:
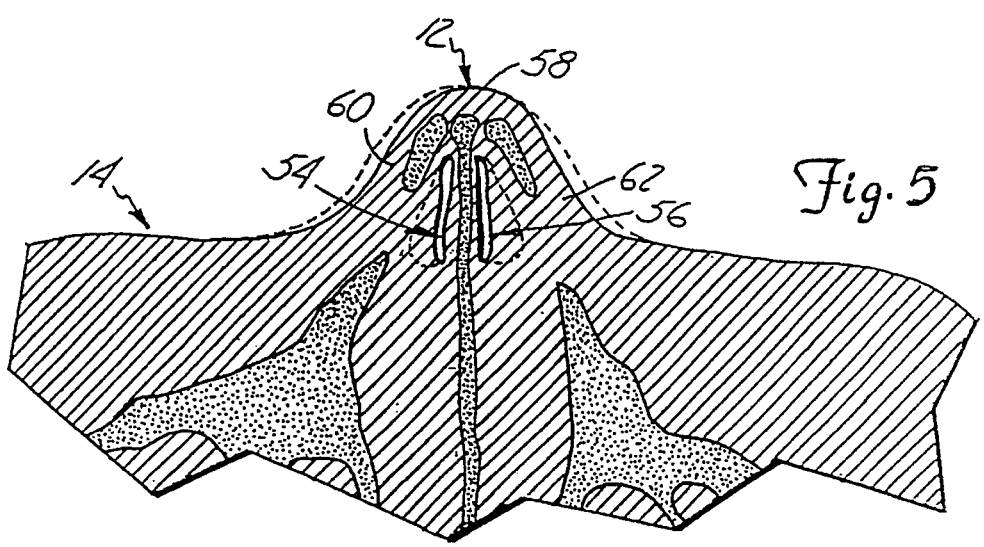
FIG. 5 shows a cross section view similar to that of FIG. 4 with a reduced air flow through the nasal passages.

During the peak of an inhalation in the breathing process, the slight decrease in pressure inside the nose leads to a slight drawing in of the outer walls of the nose. If, however, there has been an injury to the nasal passages leading to some obstructing thereof, or there is a swelling of the tissues lining those passages because of an allergic reaction or sickness, the tissues forming outer walls, 60 and 62, on the exterior sides of first and second nasal passages 54 and 56, respectively, inhalations can lead to even greater decreases in air pressure as air velocity through the narrowed passages increases as the breather attempts to get a full breath. Outer wall tissues 60 and 62 then tend to be more strongly drawn in to the nasal passages as can be seen in FIG. 5, even to the point in some circumstances of the passages collapsing to near closure. The portion of the outer wall tissues 60 and 62 so drawn in during inhalation is that located between the end of the nasal passage bone and the skull shown in a dashed line in FIGS. 1 and 3, and the entrance to nasal passages 54 and 56. Such drawings in of the outer wall tissues 60 and 62, as a result, cause further nasal blockage. The severity of this nasal blockage condition depends on how narrow the nasal valve is in the person involved. Nasal dilator 10 is provided as a remedy for this nasal blockage problem.

Figure 6:
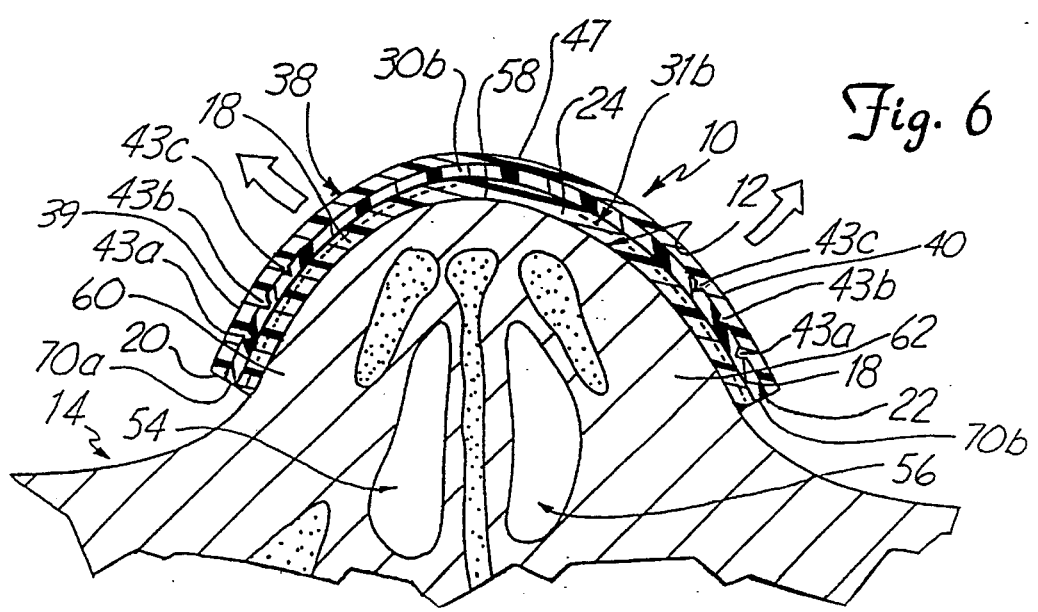
FIG. 6 shows a cross section view taken from FIG. 1 with an appreciable air flow through the nasal passages.

In use, nasal dilator 10 is engaged with the skin on outer wall tissues 60 and 62 of nose 12 by adhesive substance 46 after the removal of first and second release liners 49 and 50 therefrom. FIGS. 1 and 6 show nasal dilator 10 placed on the exterior skin of nose 12 such that intermediate segment 24 traverses bridge 58 of nose 12 with first and second end regions 20 and 22 held in contact with outer wall tissues 60 and 62 of first and second nasal passages 54 and 56, respectively, by adhesive substance 46. Adhesive substance 46 located at first and second end regions 20 and 22 of dilator 10, and at intermediate segment 24, releasably engages unitary, or single body, truss member 16 to outer wall tissues 60 and 62 and bridge 58 of nose 12.

The resiliency of first and second resilient bands 30a and 30b, the tendency of these bands to return to their normally planar state once having the ends thereof forced toward one another, provides an outward pull on outer wall tissues 60 and 62 when nasal dilator 10 is properly positioned on nose 12. This outward pull counters the drawing in force on outer wall tissues 60 and 62 during inhalation, and so acts to stabilize the position of those wall tissues 60 and 62 during such inhalations. The flexibility of base material 18, interface adhesive materials 31a and 31b, and top material 38, along with the resiliency of first and second resilient bands 30a and 30b together with the flexibility they exhibit due to having a relatively slight thickness, all allow nasal dilator 10 to closely conform about the curves of nose 12 of each individual wearer to increase the comfort of that person during use. The relatively slight thickness of resilient bands 30a and 30b also enhances the axial torsional flexibility of truss member 16 about the longitudinal extent thereof which further increases wearer comfort and aids in maintaining adhesion of adhesive substance 46 to the wearer's nose.

Further, the spun-laced fabric structure of the fabric strip serving as base material strip 18 permits limited, primarily plastic but somewhat elastic, deformation within the thickness of base material 18. This deformation property spreads out through that strip delaminating forces such as may be caused by (1) the inherent tendency of resilient bands 30a and 30b to return to their normally planar state, (2) surface configuration differences between those resilient bands and nose 12 of a wearer, and (3) displacement of unitary, or single body, truss member 16 relative to outer wall tissues 60 and 62 as a result of shear, tensile, cleavage or peel forces imparted at or to those outer wall tissues and truss member 16 due to wearer skin movement (e.g. nose gestures) or contact with an exterior object such as a pillow. Such delaminating forces tend to cause nasal dilator 10 to be inadvertently detached from nose 12 of a wearer. In spreading out these delaminating forces, base material strip 18 acts as a mechanical buffer to prevent transfers of focused forces to adhesive substance 46, and so to the skin of nose 12 of the wearer. Providing the transfer of focused delaminating forces substantially eliminates itching sensations caused by the separation of adhesive substance 46 from portions of the skin under dilator 10 that a wearer 14 may experience if such delaminating forces were focused at the skin of nose 12.

The range of dilating force provided by dilator 10, that is, the outward pull provided to outer wall tissues 60 and 62 by the resiliency of truss member 16 due to resilient bands 30a and 30b therein has been found to have a suitable range of from 5 to 50 grams or more. Under 10 grams of such dilating force is usually insufficient to help most wearers with any significant degree of nasal blockage during inhalations. However, if the nasal blockage is mild enough, a positive effect may be noticed by the wearer with as little as 5 grams of dilating force provided by dilator 10. A dilating force in excess of 40 grams is often somewhat obtrusive and uncomfortable for many wearers, though not all, wearers of such a dilator.

As a result, nasal dilator 10 is fabricated to provided typically from 20 to 30 grams of dilating spring force on outer walls 60 and 62 of nasal passages 54 and 56, at least at locations inwardly from notches 43a, 43b and 43c along resilient bands 30a and 30b. Each of these resilient bands provides a portion of this total. The dilating spring force at these notches out to the ends of dilator 10 are progressively reduced as described above to thereby reduce the peel forces experienced at the ends of dilator 10. Since the two resilient bands 30a and 30b used in unitary, or single body, truss member 16 are generally of equal proportions with generally similarly located and sized notches 43a, 43b and 43c provided therein, each of bands 30a and 30b provide approximately one-half of the total dilating spring force occurring at each location along the length of dilator 10, but could be of different widths or lengths to allow varying of the dilating force along the length of the nose.

As can be best seen in FIGS. 1 and 6, unitary truss member 16, comprising base material strip 18, interface adhesive material strips 31a and 31b, top material 38, and first and second resilient bands 30a and 30b, include a first scalloped edge, 70a, at one end, and a second scalloped edge, 70b, at the opposite end of that member. First scalloped end edge 70a is formed by first end region 20 of base material strip 18 and first end region 39 of top material 38, and by first ends 41a and 41b of resilient bands 30a and 30b, and first ends 33a and 33b of adhesive strips 31a and 31b. Second scalloped end edge 70b is formed by second end region 22 of base material strip 18 and second end region 40 of top material 38, and by second ends 42a and 42b of first and second resilient bands 30a and 30b, and by second ends 34a and 34b of adhesive strips 31a and 31b. Because of the similarity of first and second scalloped end edges 70a and 70b, only one need be described to understand both which will be first scalloped end edge 70a.

First scalloped end edge 70a includes two protrusions, 72a and 74a, separated by a setback portion, 76a. The protrusion extent of protrusion 72a and 74a are set by the cutting die used in forming a dilator 10 from a continuous strip of combined materials matching the materials in a truss member 16, the protruding portions being chosen in dilator 10 to be formed by first ends 41a and 41b of resilient bands 30a and 30b, respectively, in the corresponding first ends 33a and 33b of adhesive material strips 31a and 31b. Since protrusions of the resilient bands are outermost, the die cutting a truss member 16 from a continuous strip need not waste any resilient band material. The protrusions containing resilient bands from one truss member 16 will match those from the next truss member 16 so that essentially no material need be cut out between them and lost in the fabrication process. Due to the setbacks from the protrusions contained in the resilient bands, on either side of each, that is including setback, 76a, and the material on the outer sides of the resilient bands, there will be some loss of this material at each cutting between adjacent truss member portions. However, the loss of these materials is significantly reduced in addition to the near elimination of any loss of resilient band material. Therefore, the resulting economies in the manufacturing process in using continuous resilient bands extending to the ends of the dilator are significant.

Thus, dilators can be fabricated without undue waste in a continuous fabrication operation. However, these dilators of the shown design do not result in inadvertent peeling at the ends thereof during use, that is, delamination of the end region from the skin of a wearer's nose, because of facial gestures, forces from external objects like pillows during sleep, and the like. This is because the spring constant is much reduced toward each of the opposite ends of the dilator by the notches 43a, 43b and 43c provided toward the ends of the resilient bands 30a and 30b provided in that dilator. Hence, a dilator is provided in an efficient fabrication process which permits tailoring the spring constant along the lengths thereof to desired values at various locations along that length.

As can be seen in FIG. 2, in the situation where resilient bands 30A and 30B are adhered to base material strip 18 by adhesive strips 31A and 31B, respectively, before notches 43A, 43B and 43C are cut into these resilient strips, base material strip 18 will by this adherence keep any portions of resilient bands 30A and 30B in the relative same position should the cutting of the notches go so far as to separate portions of these resilient bands form one another. This is true also even if the cutting action should sever the portion of base material strip 18 underneath the notches since the strip material extends outward from either side of these resilient strips. This retention action is supplemented by top material strip 38 if it also is adhered to resilient bands 30A and 30B prior to such notch cutting so that the notching cut is made through this top material strip, again because the strip extends past either side of these resilient bands.

However, the provision of base material strip 18 and top material strip 38 in dilator 10 results in added in added costs in fabricating that dilator. These costs are avoidable if dilator 10 is fabricated from just the resilient band material by using that material to again form just a single body structure again having a porous (needed if the band has been perforated by tiny holes to aid moisture evaporation, otherwise not), acrylic, pressure sensitive bio-compatible adhesive applied on one side thereof. This adhesive provides, as before, the engagement means for adhering the resulting dilator to the skin of wearer's nose 12 and aids in spreading out the delaminating forces tending to cause that dilator to be inadvertently detached from nose 12 of the user. However, this spreading of the delaminating forces by the adhesive will typically be insufficient to prevent peeling unless notches again are provided in some form in the resilient material forming such a dilator.

One such possible notching arrangement, which would retain the ends of the resilient band or the dilator with the rest of the dilator even though the notch extended therethrough, is to form the notches in the band so as to not reach either of the sides of the resilient material band forming the body of the dilator. This arrangement would thereby leave a portion of the band on either side of a notch between the ends of that notch and the corresponding side of the band. The band material remaining between the notch and each side of the band will, of course, exhibit a much reduced spring constant to thereby reduce the outward force present at the corresponding end of the dilator to thereby reduce the tendency of the dilator ends to peel away from the wearer's skin. However, that remaining band material will still retain in the dilator the dilator end portions, those portions of the band between each of the notches and the corresponding one of the opposite end edges, without the need for either a base material strip or a top material strip despite the notch be cut entirely through the band.

That is, this remaining band material between a notch and the sides of the band or dilator will retain the end of the band beyond the notch and will also bend quite easily to thereby reduce the peeling force at the end edge by, in effect through such bending, convening that peeling force into a sheer force which is much better resisted by the adhesive material engaging the dilator to the skin of the wearer's nose. Such notches in the resilient band forming the dilator would typically be cut at the same time the band itself was die cut out of resilient material stock to assure there would always be that small amount of remaining material between each notch and the sides of the resulting band. The band and the notches may be cut from the adhesive covered side of the band to the opposite side so that the notch sidewalls and the adhesive covered surface of the band meet at any obtuse angle to avoid a sharp edge being positioned next to the wearer's skin which could result if the cut is made from the other side.

Although such notches could be just simple "V" cuts in the band material as before, or just slits cut into the band, a significantly wider notch can be used instead extending all the way through the band but narrower in extent than the width of the band, i.e. an elongated hole in the band, such as is shown in the bottom side pictorial view of such a dilator in FIG. 7. There, dilator 10 is formed of a single resilient band strip, 80, having a porous, acrylic, pressure sensitive bio-compatible adhesive, 81, (indicated by stippling in FIG. 7) coated on what would be the bottom side thereof during use on a wearer's nose. Resilient band 80 is again formed of the same resilient polymer material used for bands 30A and 30B, an industrial grade, biaxially oriented polyester, such as MYLAR® Type A as indicated above, of a width of approximately 0.375 in. in its narrowest portion at the middle of the band and of a somewhat greater width at the ends past the indentation at the middle portion and, perhaps, a bit thinner to maintain the same effective spring constant in view of the increased width.

A pair of elongated openings, 82, or holes, are provided through adhesive 81 and resilient band 80 as the wide notches to form substantial separations between some portions of band 80, and which extend near but do not reach the sides of the band, and which are each located near one of the opposite end edges of that band. Although shown as openings completely through band 80 to thereby completely separate surrounded interior portions of that band from the rest of the band, openings 82 need not extend all the way through band 80. Even if they for the most part do extend all the way through band 80, the portions previously filling holes 82 may be left in place without removal thereof. In any of these forms, openings 82 as a result substantially separate the remaining central portion of band 80 from the end portions thereof on the opposite sides of openings 82. In addition, resilient band 80 can be perforated with a large number of tiny openings over substantial areas, or all of that band (not shown) to aid moisture developing thereunder to evaporate.

The material portions, 83, remaining between the ends of openings 82 and the sides of band 80 will retain end portions, 84, each located between a corresponding opening 82 and the nearby one of the opposite end edges of band 80. This retention of end portions 84 by material portions 83 will occur even if openings 82 continue completely through band 80. Remaining material portions 83 will also allow end portions 84 to bend sharply and relatively easily with respect to the central portions of band 80 to permit those end portions follow the contours of the sides of a user's nose without large outwardly directed forces resulting at the ends thereof. This arrangement effectively changes what would otherwise be significant peel forces at the outer ends of these end portions 84 into sheer forces that are much better resisted by adhesive 81.

FIG. 8 shows the positioning of dilator 10 of FIG. 7 on nose 12 as part of human face 14, and typically positioned there at the same location as were the previously described dilators. The version of the homogeneous single body dilator shown in FIGS. 7 and 8 shown in these figures has just one opening 82 shown located near each of the opposite ends of strip 80 to provide a reduced effective spring constant at those locations in strip 80 to result in reduced outward forces at the opposite ends of that strip. Alternatively, a series of such openings, or wide notches, can be provided near each of the opposite ends of strip 80 to provide a reduced effective spring constant at those locations in strip 80 that extends over a greater distance along the length of that strip so that the change is less abrupt. This distributed reduction in spring constant may be further adapted to a desired distribution by choosing different lengths for the openings in such a series so as to leave more or less material between the ends of the openings and the sides of the band. Thus, by having the opening 82 nearest the center of band 80 in the series thereof the shortest with each successive opening in this series toward the nearest end of band 80 being longer, the effective reduction in the spring constant can be tapered downward in value from the maximum value toward the center of that band.

Figure 10:
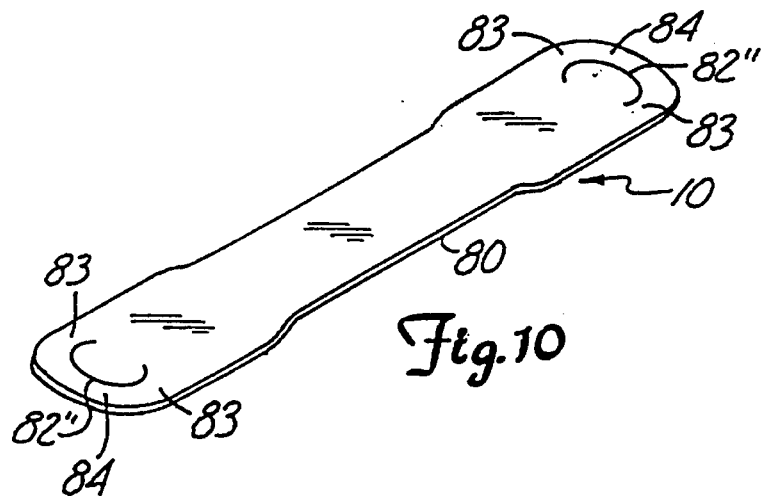
FIG. 10 shows a pictorial view of an alternate embodiment of the dilator of the present invention.
Figure 11:
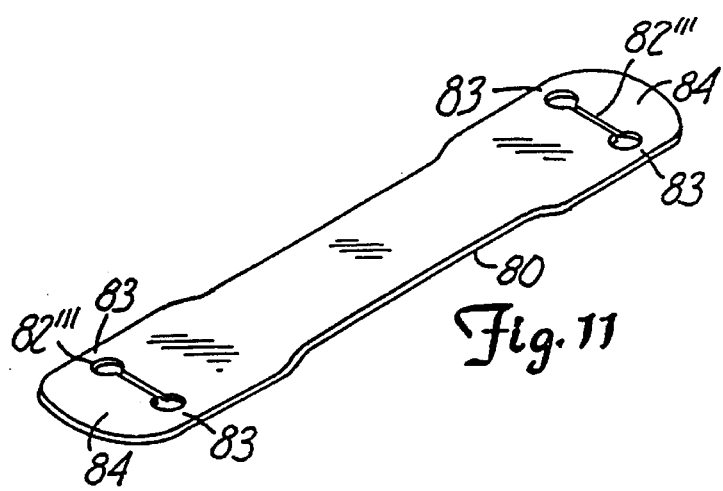
FIG. 11 shows a pictorial view of an alternate embodiment of the dilator of the present invention.

FIGS. 9, 10 and 11 show that the openings 82, or the notches, can be formed of various alternative shapes to also affect the distribution of the spring constant reduction as they are not confined to being the elongated opening shape shown for openings 82 in FIGS. 7 and 8. Thus, in FIG. 9, a top pictorial view of dilator 10 is provided showing openings or cut through notches that are alternatively shaped to those in FIGS. 7 and 8, the openings in this instance being symmetrical round holes, 82', rather than the elongated openings, or rounded end rectangular shapes, followed by openings 82 in dilator 10 of those figures.

FIGS. 10 and 11 each show a pair of cut slits as the notches rather than broader openings as the substantial separation forming the notches between the end portions and the central portion of dilator 10. FIG. 10 shows a pair of slit openings, 82", following a portion of the circular edge of openings 82' in FIG. 9 somewhat beyond half of the circle (but could follow a portion of an oval shape or of other closed curves) so as to leave the interior of the circular portion attached to the remainder of band 80 along the sides thereof closest to the center of that band. Slit openings 82" are continued past the half circle points so as to have the ends thereof point away from the sides of band 80 to thereby minimize the possibility of crack propagation from the ends of the slits to the sides of that band.

Alternatively, in FIG. 11, slits following straight lines are the substantial separations cut into band 80 but with small circular openings provided at each end thereof to thereby together provide a pair of openings, 82''', the circular opening portions provided to again prevent any crack propagation from the ends of the slits to the sides of band 80. This crack propagation is most likely to occur during the die cutting of these openings in dilator 10 rather than during use since such use usually occurs on just a single occasion for each dilator resulting in relatively little repeated flexing remaining material portions 83.

Notches or broader openings can also be used to provide increased flexibility of resilient band 80 along the length and across the width of that band in addition to providing such flexibility toward each of the opposite ends of band 80 along the width and across the length thereof as shown for dilator 10 in FIGS. 7, 9, 10 and 11. Thus, FIG. 12 shows not only a pair of elongated openings 82 substantially separating end regions 84 from the central remainder of resilient band 80 as in the dilator 10 of FIG. 7, but also shows a longitudinal opening, 85, provided transverse to and intersecting openings 82 to then extend beyond them to nearly reach the length of dilator 10 between the opposite ends thereof to thereby substantially separate side portions of band 80.

As a result, there are further remaining material portions, 86, provided between the ends of longitudinal opening 85 and the corresponding one of the opposite end edges of dilator 10. The presence of longitudinal opening 85 extending so close to the opposite end edges of dilator 10 allows the two side portions, or longitudinal subbands, 87, formed as a result of providing longitudinal opening 85, to bend sharply and relatively easily with respect to each other at remaining material portions 86 to thereby increase the flexibility of resilient band 80 across its width. In effect, subbands 87 closely approximate the behavior of resilient bands 30A and 30B in dilator 10 of FIG. 2. Again, a bottom pictorial view of dilator 10 is shown in FIG. 12 so that adhesive 81, provided on resilient band 80 at end regions 84 and subbands 87 as represented by the stippling present thereon, is exposed to view.

Figure 13:
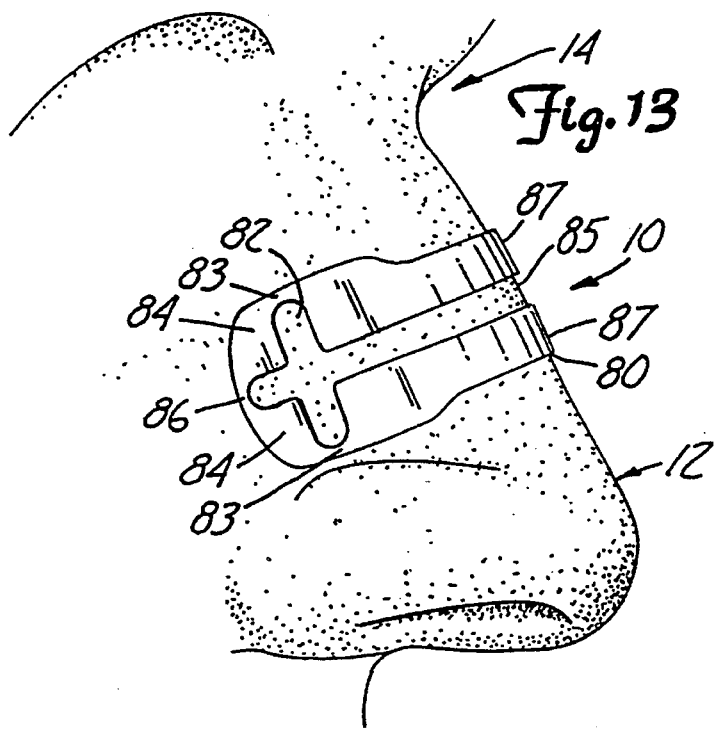
FIG. 13 shows a pictorial view of a portion of a human face including the nose, and of the dilator of FIG. 12 engaged with that nose.

FIG. 13 shows dilator 10 of FIG. 12 positioned on nose 12 seen as part of a portion of human face 14. Again, dilator 10 in FIG. 13 is typically positioned on nose 12 at the location used for previously described dilators.

Further flexibility across the width of dilator 10 can be provided by the use of an additional longitudinal opening in resilient band 80 paralleling longitudinal opening 85 in dilator 10 of FIG. 12. The result is shown in FIG. 14 where there is now shown a pair of parallel longitudinal openings, 85', provided in resilient band 80 to thereby form three subbands, 87', each of longitudinal openings 85' intersecting both members of a corresponding pair of transverse openings, 82''''. The result is to provide two small material remaining portions 83 between the sides of dilator 10 and openings 82'''' as before, and a further small material portion, 83' between those two openings 82'''' at each end of dilator 10. Similarly, there are two remaining portions of material, between the ends of each of longitudinal openings 85' and the opposite end edges of dilator 10.

Dilator 10 of FIGS. 12 and 13 can be made to approximate previously described dilators even more closely by providing a base material strip below and adhered to resilient band 80, such as the form of band 80 shown in FIG. 12, with this strip having the adhesive for engaging the user's nose applied thereon rather than on resilient band 80. Similarly, a top material strip can be supplied over resilient band 80 and adhered thereto with or without the base material strip present. The form of resilient band 80 shown in FIG. 14 can alternatively be used.

Figure 15:
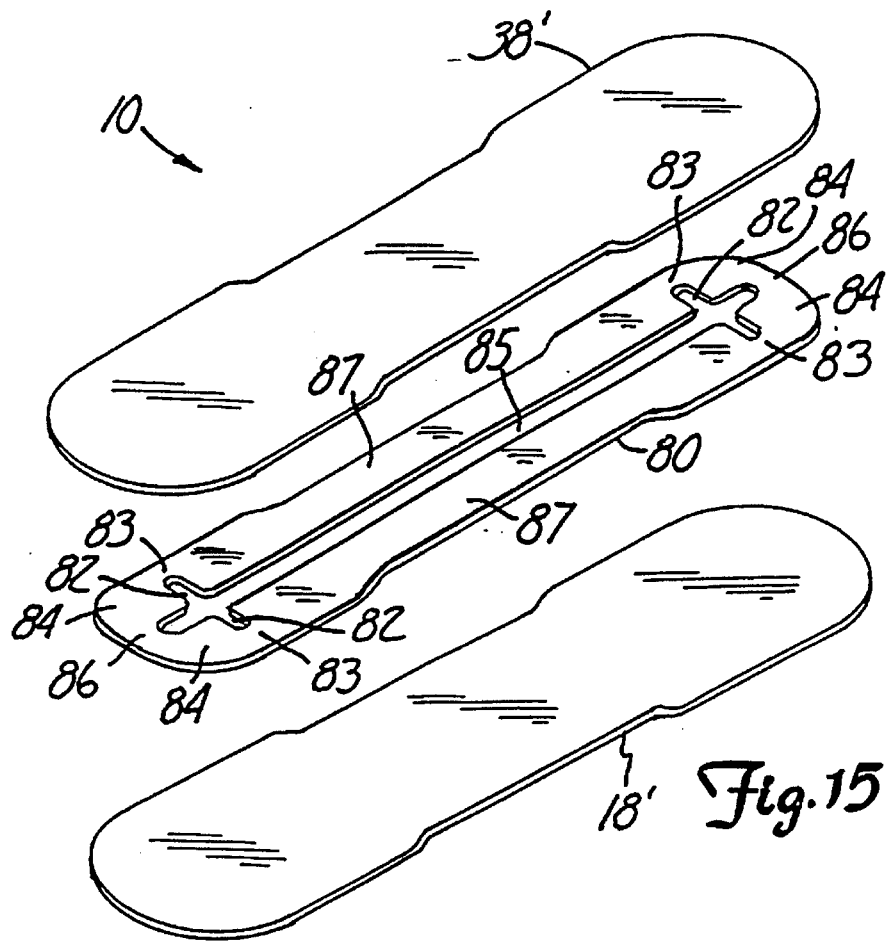
FIG. 15 shows an exploded pictorial view of an alternate embodiment of the dilator of the present invention.

An exploded pictorial view of such an arrangement is shown in FIG. 15 using the form of resilient band 80 shown in FIG. 12 except for the removal of adhesive 81 therefrom which is placed instead on the bottom side of a base material strip, 18', for engagement of the resulting dilator with nose 12 of a wearer. Resilient band 80 is adhered to base strip 18', and that structure has a top material strip, 38', adhered thereto to form a unitary or single body dilator structure now heterogeneous rather than homogeneous. Base material strip 18' can be formed of the same material described earlier for base material strip 18 of dilator 10 in FIG. 2, and top material strip 38' can be formed of the same material as was top material strip 38 in dilator 10 of FIG. 2. The same sorts of adhesives used in dilator 10 of FIG. 2 to form the components there into a single body can be used to adhere resilient band 80 to base material strip 18' and top material strip 38'. That is, typically, either a porous, acrylic, pressure sensitive bio-compatible adhesive placed by coating methods, or an acrylic, pressure sensitive bio-compatible transfer adhesive material can be used.

Figure 16:
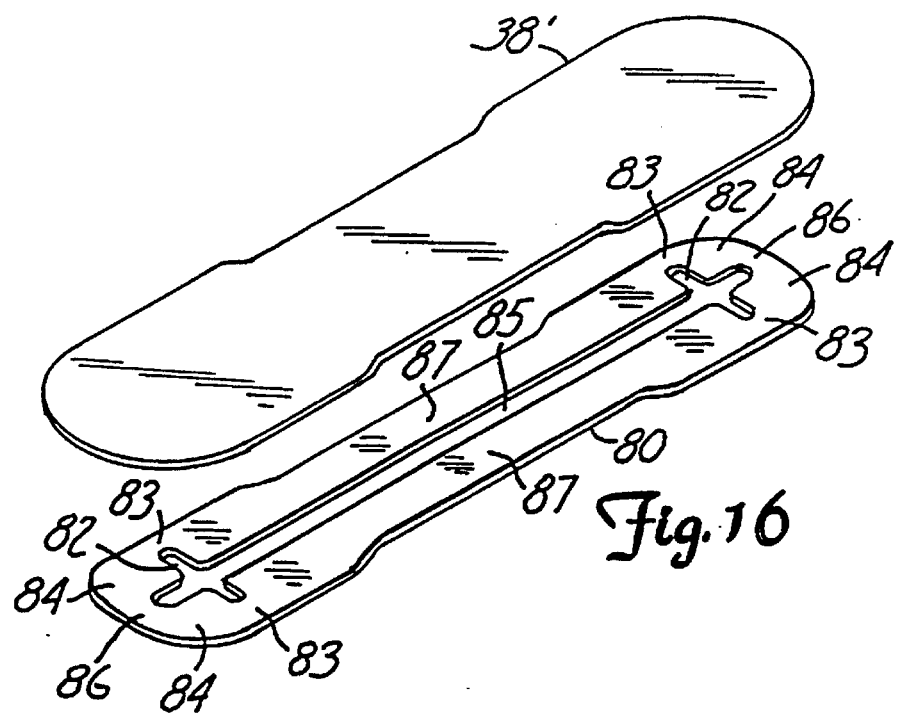
FIG. 16 shows an exploded pictorial view of an alternate embodiment of the dilator of the present invention.

Alternatively, dilator 10 of FIG. 12 can be used just as disclosed there, including having adhesive 81 on the bottom side thereof, if just top material strip 38' is adhered to resilient band 80, an arrangement shown in an exploded pictorial view in FIG. 16. Similarly, resilient band 80 can be adhered to just bottom material strip 18' omitting the use of to material strip 38', a structure not shown. Again, the same sorts of adhesives used in dilator 10 of FIG. 2 to form the components there into a single body can be used. The dilator structures of FIGS. 15 and 16 can have top material strip 38' coextensive with the outer edges of resilient band 80, or exceeding the dimensions of resilient band 80 to extend beyond the end edges thereof, or beyond the sides thereof, or both. The dilator structure of FIG. 15 can similarly have bottom material strip 18' coextensive with the outer edges of resilient band 80, or exceeding the dimensions of resilient band 80 to extend beyond the end edges thereof, or beyond the sides thereof, or both.

Figure 17:
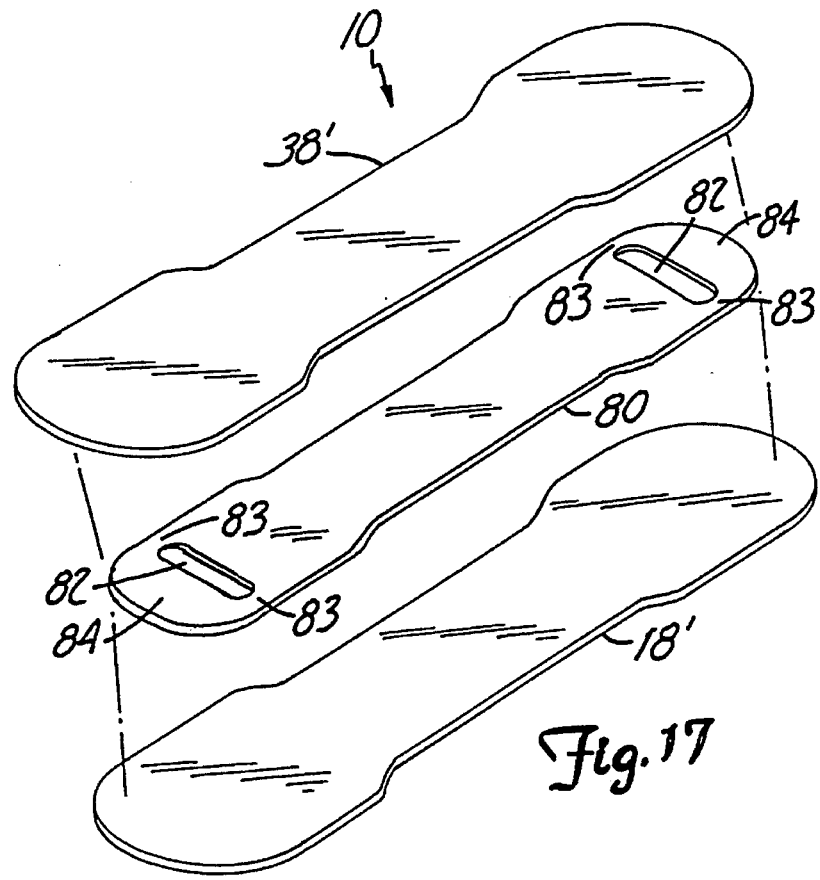
FIG. 17 shows an exploded pictorial view of an alternate embodiment of the dilator of the present invention.
Figure 18:
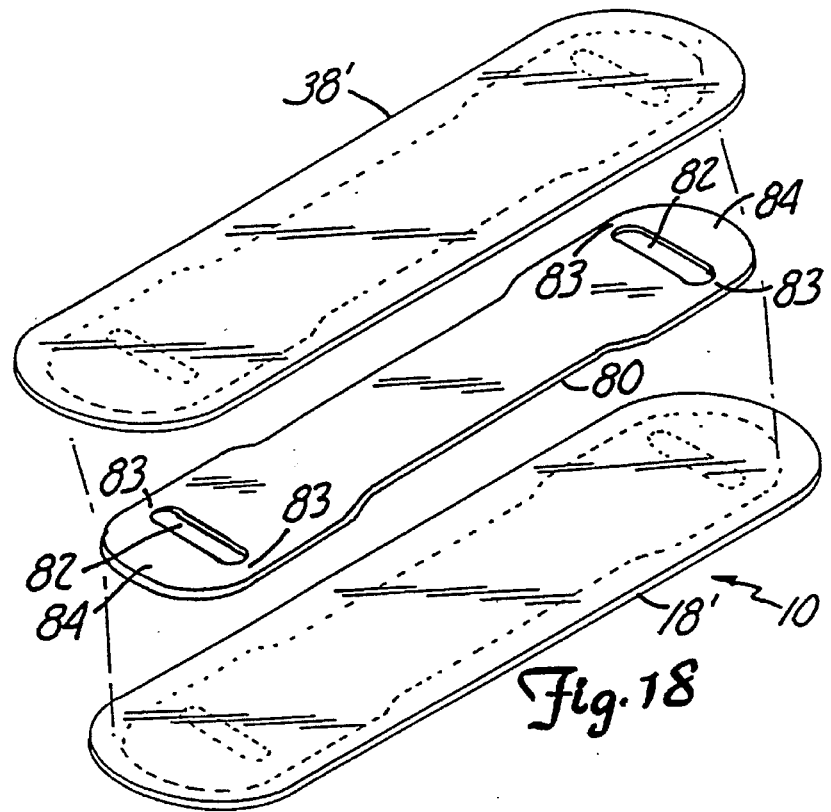
FIG. 18 shows an exploded pictorial view of an alternate embodiment of the dilator of the present invention.

Similar arrangements can be provided for dilators 10 of FIGS. 7, 9, 10 and 11 if the benefits of using a bottom material strip for spreading out the delaminating forces and the stabilizing value of a top material strip are desired in connection with the use of resilient band 80 from those figures. Thus, FIGS. 17 and 18 show the use of the form of resilient band 80 from FIG. 7 with adhesive 81 moved from resilient band 80 to the bottom of bottom material strip 18' to be used to engage the skin of a wearer's nose. In the exploded pictorial views of these figures, resilient material strip 80 with openings 82 at the opposite ends thereof is provided between and adhered to bottom material strip 18' and top material strip 38'. In FIG. 17, bottom material strip 18' and top material strip 38' are shown to be coextensive with resilient band 80, but these strips exceed the dimensions of resilient band 80 in the structure shown in FIG. 18.

Figure 19:
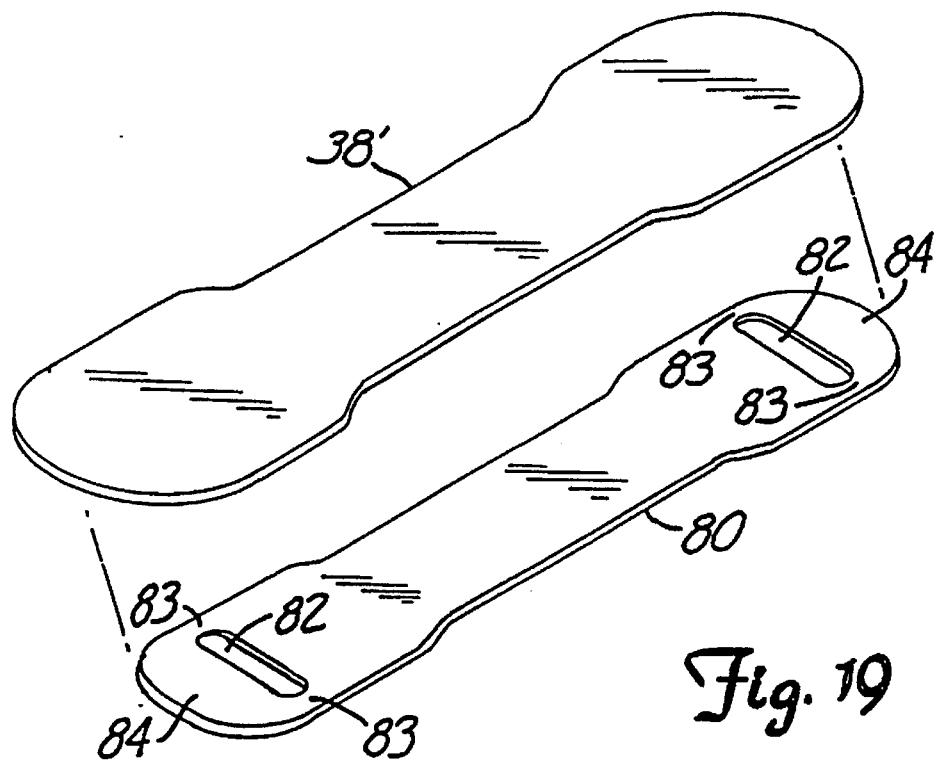
FIG. 19 shows an exploded pictorial view of an alternate embodiment of the dilator of the present invention.
Figure 20:
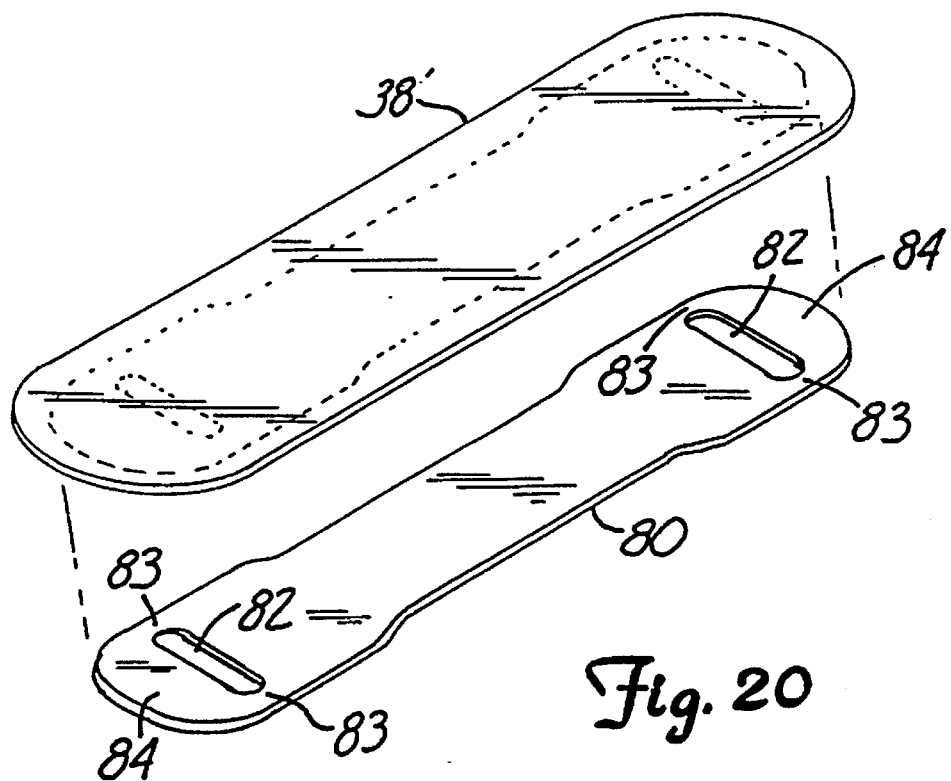
FIG. 20 shows an exploded pictorial view of an alternate embodiment of the dilator of the present invention.

Again, dilators 10 in the forms shown in FIGS. 7, 9, 10 and 11 can be used as disclosed there with adhesive 81 applied to the bottom side thereof for engaging a wearer's nose by omitting the use of base material strip 18' from the structures shown in FIGS. 17 and 18 for any of those forms of resilient band 80 used in these structures. This leaves just top material strip 38' adhered to resilient band 80, an example of which is shown in FIGS. 19 and 20 using the form of resilient band 80 shown in FIG. 7. Again, FIG. 19 shows an exploded pictorial view of top material strip 38' having dimensions coextensive with those of the outer edges of resilient band 80, and FIG. 20 shows an exploded pictorial view of top material strip 38' with dimensions exceeding those of the outer edges of resilient band 80 to extend therebeyond both in length and in width.

Figure 21:
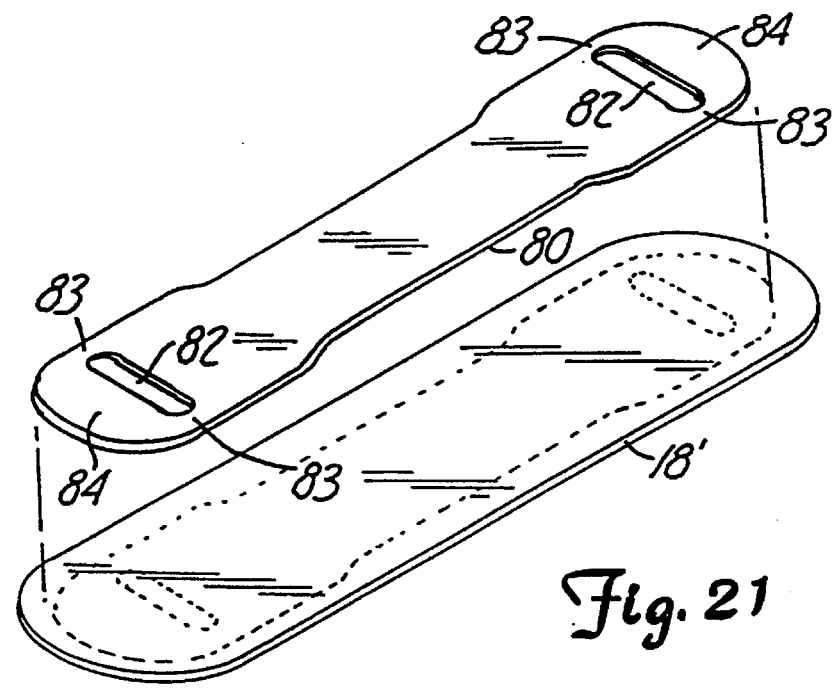
FIG. 21 shows an exploded pictorial view of an alternate embodiment of the dilator of the present invention.
Figure 22:
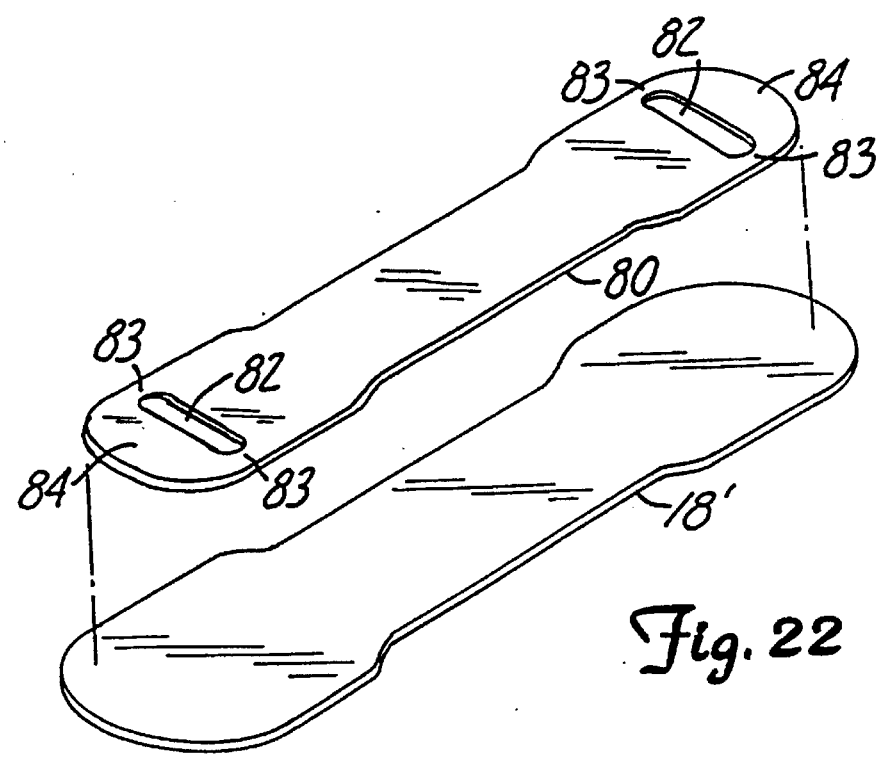
FIG. 22 shows an exploded pictorial view of an alternate embodiment of the dilator of the present invention.

The alternative is again possible of omitting top material strip 38' from the structures shown in FIGS. 17 and 18 but retaining the use of bottom material strip 18', and having adhesive 81 moved from any of the forms of resilient bands 80 shown in FIGS. 7, 9, 10 and 11 used in these structures to the bottom of base material strip 18' for use in engaging the nose of a wearer. In FIGS. 21 and 22, exploded pictorial views are shown of this arrangement based again on the use of the form of resilient band 80 shown in FIG. 7 adhered to bottom material strip 18' having the skin engaging adhesive on the opposite side thereof. Bottom strip 18' is coextensive with resilient band 80 in the view shown in FIG. 21, but bottom material strip 18' exceeds the dimensions of resilient strip 80 in FIG. 22 both in length and in width. Here again, the same sorts of adhesives used in dilator 10 of FIG. 2 to form the components there into a single body can be used in the structures described in connection with FIGS. 17 through 22.

Although the present invention has been described with reference to preferred embodiments, workers skilled in the art will recognize that changes may be made in form and detail without departing from the spirit and scope of the invention.

What is claimed is:

1. A dilator capable of introducing separating stresses in anatomical outer wall tissues, said dilator comprising:

a truss having a pair of spaced-apart end surfaces terminated by end edges at opposite ends of said truss and having means for generating restoring forces including at least a first resilient band of selected thickness in said truss extending between said end edges such that, if said spaced-apart end surfaces are forced toward one another from initial positions to thereby substantially reduce direct spacing therebetween by a spacing reduction force external to said truss, restoring forces result in said truss which tend to restore said direct spacing between said end surfaces with such restoring forces being due to at least said first resilient band, and further having means for reducing said restoring forces at a selected location in said first resilient band comprising a separation at said selected location between selected portions of said first resilient band with said separation surrounded by a corresponding separation edge thereabout intersecting at least a first surface of said first resilient band; and engagement means adhered to said end surfaces adapted for engaging exposed surfaces of outer wall tissues and for remaining so engaged against said restoring forces.

2. The dilator of claim 1 wherein said separation has said corresponding separation edge thereabout intersecting at least in part a second surface of said first resilient band on a side thereof opposite that at which said first surface occurs.

3. The dilator of claim 2 wherein said separation edge has portions thereof across said separation from one another spaced apart such that said separation is formed at least in part as an opening in said first resilient band.

4. The dilator of claim 2 wherein said separation edge has portions thereof across said separation from one another adjacent one another such that said separation is formed at least in part as a slit in said first resilient band.

5. The dilator of claim 1 wherein said first resilient band is bounded at a first end thereof by a said end edge and by two side edges between which said separation occurs such that corresponding portions of said separation edge thereabout are parallel to each of said side edges substantially where said separation edge comes closest thereto.

6. The dilator of claim 5 wherein there is a plurality of separations at selected locations in said first resilient band between selected portions thereof with each said separation surrounded by a corresponding separation edge thereabout intersecting at least said first surface, said first resilient band being bounded at an opposite end thereof by that remaining said end edge and by two further side edges between which another said separation in said plurality thereof occurs such that corresponding portions of said separation edge thereabout are parallel to each of said two further side edges substantially where that said separation edge comes closest thereto.

7. The dilator of claim 1 wherein said truss has a cover flexible strip therein with said first resilient band positioned at least in part between said cover flexible strip and any exposed surfaces of outer wall tissues so engaged.

8. The dilator of claim 7 wherein said cover flexible strip is longer than said first resilient band.

9. The dilator of claim 7 wherein said cover flexible strip has a length substantially equal to that of said first resilient band.

10. The dilator of claim 7 wherein said truss has a base flexible strip therein with said position at least in part between said first resilient band and any exposed surfaces of outer wall tissues so engaged.

11. The dilator of claim 1 wherein said truss has a base flexible strip therein with said position at least in part between said first resilient band and any exposed surfaces of outer wall tissues so engaged.

12. The dilator of claim 11 wherein said base flexible strip is longer than said first resilient band.

13. The dilator of claim 11 wherein said base flexible strip is shorter than said first resilient band.

14. The dilator of claim 11 wherein said base flexible strip has a length substantially equal to that of said first resilient band.

15. The dilator of claim 1 wherein said first resilient band is entirely of a shaped sheet of at least partially perforated polymer material.

16. The dilator of claim 1 wherein said separation edge has two longitudinal portions thereof extending substantially parallel to one another along a longitudinal direction between said end edges of said truss and joining transverse edge portions of said separating edge at each opposite end thereof extending in a direction transverse to said longitudinal direction.

17. The dilator of claim 16 wherein there is a plurality of separations at selected locations in said first resilient band between selected portions thereof with each said separation surrounded by a corresponding separation edge thereabout intersecting at least said first surface, said separation edges in said plurality thereof each having two longitudinal portions thereof extending substantially parallel to one another along a longitudinal direction between said end edges of said truss and joining transverse edge portions of said separating edge at each opposite end thereof extending in a direction transverse to said longitudinal direction.

18. The dilator of claim 1 wherein there is a plurality of separations at selected locations in said first resilient band between selected portions thereof with each said separation surrounded by a corresponding separation edge thereabout intersecting at least said first surface.

* * * * *

UNITED STATES PATENT AND TRADEMARK OFFICE
CERTIFICATE OF CORRECTION

PATENT NO. : 5,611,333

DATED : MARCH 18, 1997

INVENTOR(S) : BRUCE C. JOHNSON

It is certified that error appears in the above-indentified patent and that said Letters Patent is hereby corrected as shown below:

Col. 6, line 49, delete "stone", insert --some--

Col. 10, line 50, delete "convening", insert --converting--

Col. 13, line 23, after "material", insert --86',--

Signed and Sealed this

Twenty-sixth Day of August, 1997

Attest:

BRUCE LEHMAN

Attesting Officer

Commissioner of Patents and Trademarks